(12) United States Patent
Otsubo et al.

(10) Patent No.: US 7,112,189 B2
(45) Date of Patent: Sep. 26, 2006

(54) PANTS-TYPE DISPOSABLE WEARING ARTICLE

(75) Inventors: Toshifumi Otsubo, Kagawa-ken (JP); Shunsuke Takino, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 50 days.

(21) Appl. No.: 10/839,707

(22) Filed: May 6, 2004

(65) Prior Publication Data

US 2005/0004544 A1    Jan. 6, 2005

Related U.S. Application Data

(63) Continuation of application No. PCT/JP03/01243, filed on Feb. 6, 2003.

(30) Foreign Application Priority Data

Feb. 8, 2002    (JP) .............................. 2002-032601

(51) Int. Cl.
*A61F 13/15* (2006.01)
(52) U.S. Cl. ............. 604/201; 604/385.21; 604/385.01
(58) Field of Classification Search ......... 604/385.201, 604/385.01, 385.21, 385.24, 385.25, 385.26
See application file for complete search history.

(56) References Cited

U.S. PATENT DOCUMENTS

| | | | | |
|---|---|---|---|---|
| 3,710,797 A | * | 1/1973 | Marsan ................. | 604/385.201 |
| 3,744,494 A | * | 7/1973 | Marsan ....................... | 604/378 |
| 3,774,610 A | * | 11/1973 | Eckert et al. ............... | 604/365 |
| 3,848,595 A | * | 11/1974 | Endres ................. | 604/385.201 |
| 3,924,627 A | * | 12/1975 | Nystrand ..................... | 604/365 |
| 3,968,799 A | * | 7/1976 | Schrading ................... | 604/365 |

FOREIGN PATENT DOCUMENTS

| | | |
|---|---|---|
| JP | 47-36734 | 12/1972 |
| JP | 48-20638 | 3/1973 |
| JP | 50-21845 | 3/1975 |
| JP | 50-33044 | 3/1975 |
| JP | 63-32516 | 3/1988 |
| JP | 11-104177 | 4/1999 |
| JP | 11-104180 | 4/1999 |
| JP | 11-155904 | 6/1999 |
| JP | 11-169403 | 6/1999 |
| JP | 2002-035033 | 5/2002 |
| JP | 2003-010244 | 1/2003 |

\* cited by examiner

*Primary Examiner*—Jacqueline F. Stephens
(74) *Attorney, Agent, or Firm*—Lowe Hauptman & Berner LLP

(57) ABSTRACT

A pants-type disposable wearing article includes a liquid-pervious topsheet, a liquid-impervious backsheet, a liquid-absorbent panel interposed between these sheets and a liquid-impervious outer sheet lying on the outer side of the backsheet, and having a waist-hole and leg-holes. This article has a first folding guide formed in left half of the crotch region, a second folding guide formed in right half of the crotch region and third folding guides transversely extending between the first and second folding guides so that first and second regions of the crotch region are folded along the first and second folding guides so as to be tucked toward inner sides of the respective leg-holes and the third region of the crotch region is folded along the third folding guides so as to be tucked toward the waist-hole.

20 Claims, 14 Drawing Sheets

PANTS-TYPE DISPOSABLE WEARING ARTICLE

This application is a continuation of International Application No. PCT/JP03/01243 filed Feb. 6, 2003, which claims priority to Japanese Application No. 2002-032601 filed Feb. 8, 2002, all of which are hereby incorporated by reference herein in their entirety.

BACKGROUND OF THE INVENTION

This invention relates to a pants-type disposable wearing article for absorption and containment of bodily discharges.

Conventional pants-type disposable wearing articles comprise a liquid-pervious topsheet, a liquid-impervious backsheet and a liquid-absorbent panel interposed between these two sheets so as to define front and rear waist regions opposed to each other and a crotch region extending between these waist regions. The front and rear waist regions are connected to each other along transversely opposite side edge portions of these waist regions which are overlaid to form a waist-hole and a pair of leg-holes.

The leg-holes are surrounded by associated leg-surrounding flaps extending along outer edges of the associated side edge portions of the panel in a leg-surrounding direction. The leg-surrounding flaps have free side edge portions curving inwardly in a transverse direction from tops toward bottoms of the associated leg-holes so that a transverse dimension between the free side edge portions is minimized in the vicinity of the bottoms of the respective leg-holes. In this article of well known art, a transverse dimension of the crotch region is smaller than a transverse dimension each of the front and rear waist regions has. In other words, with the front and rear waist regions disconnected from each other and then developed, the article has a hourglass-like planar shape. Such pants-type wearing articles are disclosed, for example, in Japanese Patent Unexamined Publication Nos. 1999-104177A; 1999-104180A; 1999-155904A; and 1999-169403A.

When the above-cited wearing article of well known art is viewed from above the waist-hole being opened, it is found that the leg-holes are opened in the transverse direction of the article while the waist-hole is opened in the longitudinal direction of the article. With a consequence, the waist-hole is not in alignment with the leg-holes and the leg-surrounding flaps extending in the vicinity of the bottoms of the respective leg-holes lie ahead of the waist-hole. In the case of this article, there is an anxiety that the wearer's toes and/or heels might get stuck with the leg-surrounding flaps lying in the vicinity of the bottoms of the leg-holes as the wearer intends to guide his or her legs through the waist-hole then through the leg-holes. As a result, it is likely that the operation of wearing the article might be inconveniently retarded.

In this article, a transverse dimension of the crotch region in the vicinity of the bottoms of the respective leg-holes is larger than a transverse dimension of the wearer's crotch and the crotch region of the article can not be fitly put in the crotch of the wearer after the article has been put on the wearer's body. Consequently, the crotch region of the article becomes bulky and creates an uncomfortable feeling against the wearer. With the article, the leg-surrounding flaps are irregularly folded or the panel is formed with a plurality of irregular wrinkles as the crotch region of the article is squeezed in the crotch region of the wearer. These folds or wrinkles may sometimes deteriorate an excretion absorbing function in the crotch region and even allow the excretion to leak from the crotch region.

The transverse dimension of the wearer's crotch is generally in a range of 3–8 cm. In many of the articles on the market, the minimum dimension of the panel in the crotch region is generally in a range of 10–20 cm and the minimum dimension between the transversely opposite free outer side edge portions of the leg-surrounding flaps in the crotch region is generally in a range of 15–30 cm. In the articles on the market, therefore, the transverse dimension of the crotch region in the vicinity of the bottoms of the respective leg-holes is larger than the transverse dimension of the wearer's crotch.

SUMMARY OF THE INVENTION

It is an object of this invention to provide a pants-type disposable wearing article having its crotch region adapted to be fitly put in the wearer's crotch so that the article can be put on the wearer's body without being retarded and can be free from creating an uncomfortable feeling against the wearer.

According to this invention, there is provided a pants-type disposable wearing article having front and rear waist regions opposed to each other and a crotch region extending between these waist regions, the article comprising a liquid-pervious sheet, a liquid-impervious sheet and a liquid-absorbent panel interposed between these sheets and extending over the crotch region into the front and rear waist regions so as to define a waist-hole enclosed by waist ends extending in a waist-surrounding direction and left and right leg-holes respectively enclosed by leg-surrounding side edge portions extending in a leg-surrounding direction.

The article according to this invention further comprises a first folding guide extending in a left half of the crotch region from a free edge of the leg-surrounding side edge portion lying in the vicinity of a top of the left leg-hole so as to define a convexity toward a transversely middle zone of the crotch region, a second folding guide extending in right half of the crotch region from a free edge of the leg-surrounding side edge portion lying in the vicinity of a top of the right leg-hole so as to define a convexity toward a transversely middle zone of the crotch region and a pair of third folding guides spaced from and opposed to each other in the leg-surrounding direction and transversely extending between the first and second folding guides; a first region extending between the first folding guide and the free edge of the leg-surrounding side edge portion, a second region extending between the second folding guide and the free edge of the leg-surrounding side edge portion and a third region contoured by the first and second folding guides and the third folding guides in the crotch region; and the first region and the second region folded along the first folding guide and the second folding guide to be tucked toward inner sides of the left and right leg-holes and the third region is folded along the third folding guides to be tucked inwardly of the article toward the waist-hole.

This invention includes the following embodiments. The third folding guides are formed in the transversely middle zone of the crotch region.

The crotch region is formed in its transversely middle zone with a low stiffness zone so that the panel has a stiffness lower in this low stiffness zone than in other zone of the panel.

The crotch region is formed in its transversely middle zone with a panel-free zone.

The free edges of the leg-surrounding side edge portions curve inwardly from the tops to bottoms of the leg-holes so that a transverse dimension between these free edges of the side edges is minimized at the bottoms of the leg-holes.

The minimum spacing dimension between the free edges of the leg-surrounding side edge portions at the bottoms of the leg-holes is in a range of 3–9 cm after the first and second regions have been tucked.

The article further includes a pair of fourth folding guides extending inside transversely opposite side edges of the panel in the leg-surrounding direction between the third folding guides and a front end of the panel lying in the front waist region, and the fourth folding guides are defined by low stiffness zones in which the panel has a stiffness lower than in other zone of the panel or by panel-free zones provided in the panel.

The article further includes a pair of fifth folding guides extending inside the transversely opposite side edges of the panel in the leg-surrounding direction between the third folding guides and a rear end of the panel lying in the rear waist region, and the fifth folding guides are defined by low stiffness zones in which the panel has a stiffness lower than in other zone of the panel or by panel-free zones provided in the panel.

DETAILED DESCRIPTION OF THE PREFERRED EMBODIMENTS

Details of a pants-type disposable wearing article according to this invention will be more fully understood from the description given hereunder in reference to the accompanying drawings.

Figure 1:
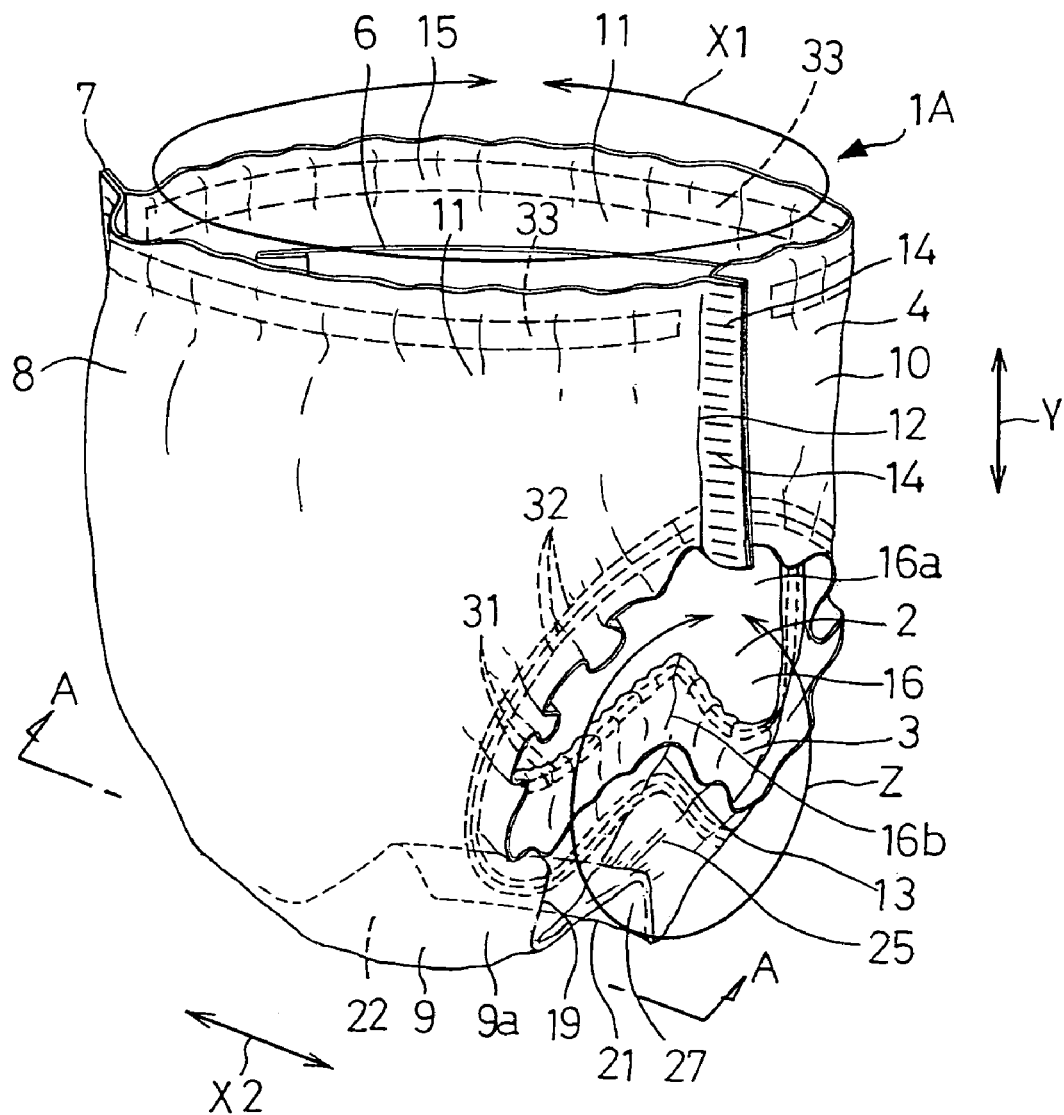
FIG. 1 is a perspective view showing a disposable wearing article according to this invention.
Figure 2:
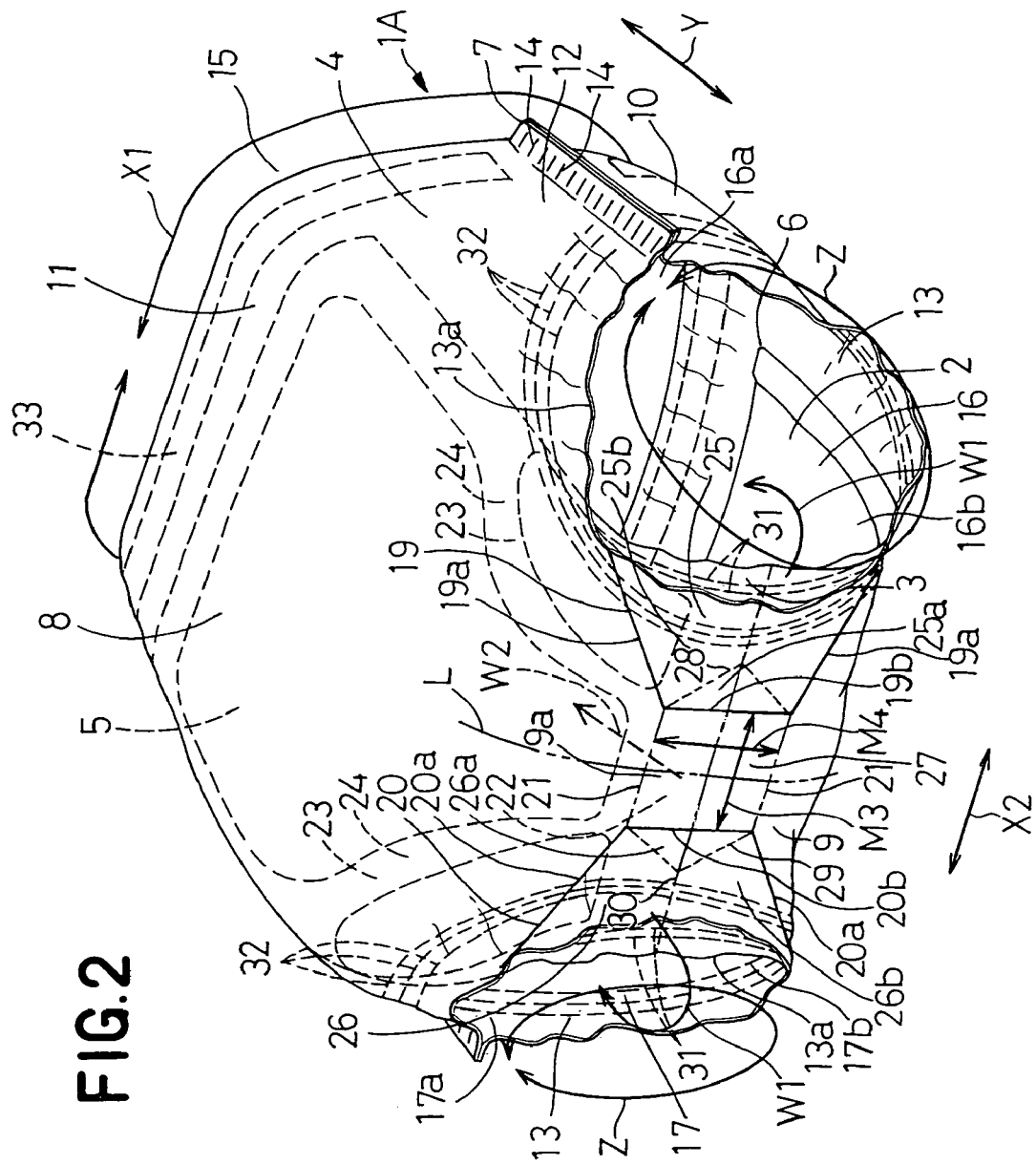
FIG. 2 is a perspective view showing the article prior to tucking of the first–third regions.
Figure 3:
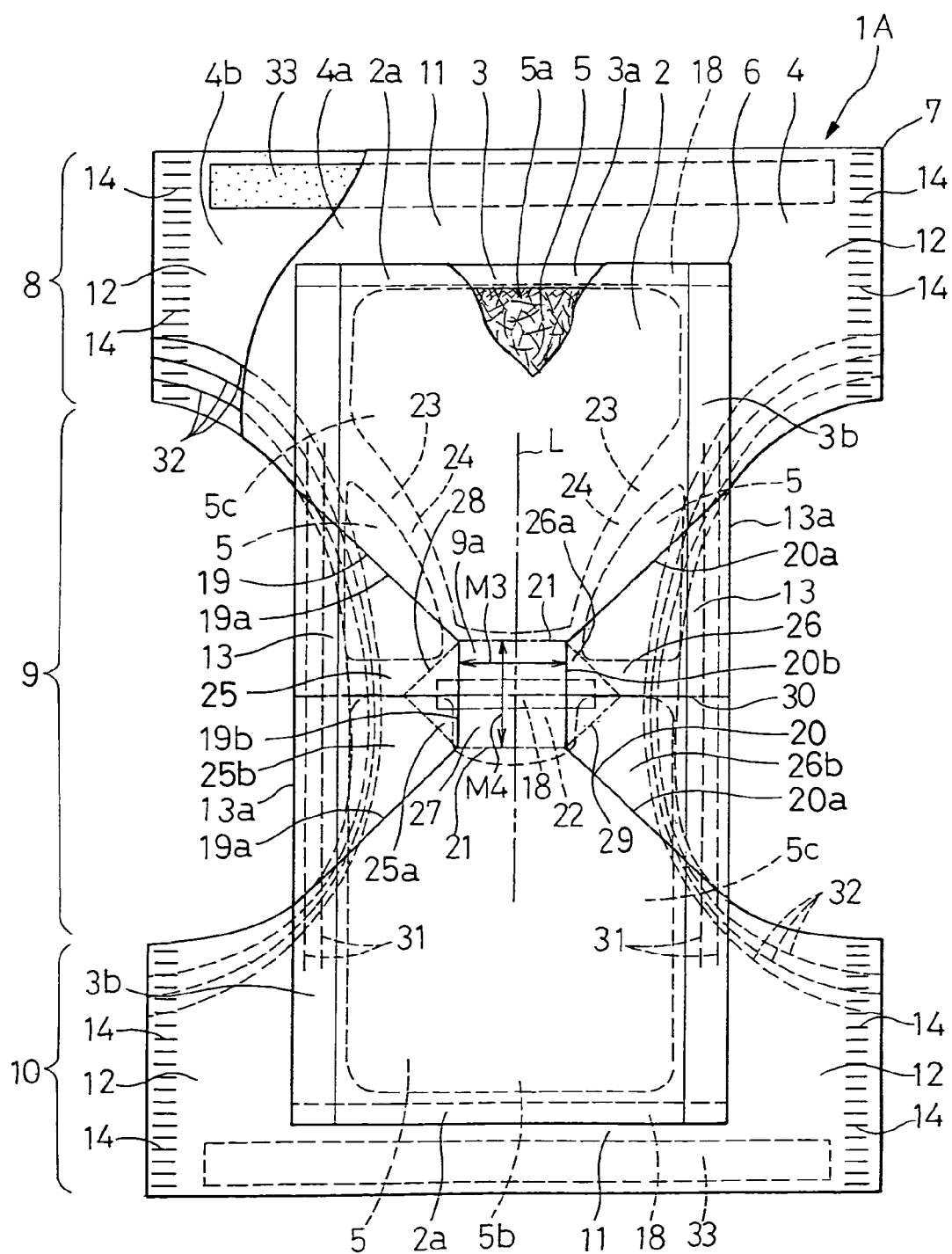
FIG. 3 is a partially cutaway developed plan view showing the article of FIG. 2 with the front and rear waist regions disconnected from each other.

FIG. 1 is a perspective view showing a disposable wearing article 1A, FIG. 2 is a perspective view showing the article 1A as before first–third regions 25, 26, 27 are tucked inwardly and FIG. 3 is a partially cutaway developed plan view showing the article 1A of FIG. 2 with front and rear waist regions 8, 10 disconnected from each other. Referring to FIGS. 1 and 2, a waist-surrounding direction is indicated by an arrow X1, a transverse direction is indicated by an arrow X2, a longitudinal direction is indicated by an arrow Y and a leg-surrounding direction is indicated by an arrow Z. Referring to FIGS. 2 and 3, first and second folding guides 19, 20 are indicated by solid lines and third folding guide 21 are indicated by dashed lines. Expression "inner surfaces of a topsheet 2, a backsheet 3 and an outer sheet 4, respectively" should be understood to be the surfaces of these sheets facing a panel 5 and expression "outer surfaces of these sheets 2, 3, 4" should be understood to be the surfaces of these sheets facing away from the panel 5.

The article 1A comprises the liquid-pervious topsheet 2 (liquid-pervious sheet) facing a wearer's body, the liquid-impervious backsheet 3. (liquid-impervious sheet) facing away from the wearer's body, a liquid-impervious outer sheet 4 (liquid-impervious sheet) lying outside the backsheet 3 and having an area larger than both the top- and backsheets 2, 3, and a liquid-absorbent panel 5 interposed between the top- and backsheets 2, 3 and firmly attached to the inner surface of at least one of these sheets 2, 3. In the article 1A, the top- and backsheets 2, 3 cooperate with the panel 5 to define a rectangular liquid-absorbent pad 6, and the outer sheet 4 defines pants 7.

The article 1A is composed of front and rear waist regions 8, 10 opposed to each other and a crotch region 9 extending between these two waist regions 8, 10. The article 1A has waist-end portions 11 of the front and rear waist regions 8, 10, respectively, extending in the waist-surrounding direction outside longitudinally opposite ends 5a, 5b of the panel 5, respectively, transversely opposite side edge portions 12 of the front and rear waist regions 8, 10, respectively, extending in the longitudinal direction outside transversely opposite side edges 5c of the panel 5, and leg-surrounding side edge portions 13 of the crotch region 9 extending in the leg-surrounding direction outside the transversely opposite side edges 5c of the panel 5 in the leg-surrounding direction.

In the article 1A, the side edge portions 13 of the respective waist regions 8, 10 are overlaid and joined at a plurality of heat-sealing lines 14 arranged intermittently in the longitudinal direction along the respective side edge portions 13. In the article 1A, a waist-hole 15 is surrounded by waist-end portions 11 and a pair of leg-holes 16, 17 are surrounded by the respective leg-surrounding side edge portions 13.

In the front and rear waist regions 8, 10 as well as in a transversely middle zone 9a of the crotch region 9, the outer surface of the backsheet 3 is firmly bonded to the inner surface of the outer sheet 4 by means of an adhesive 18. Free edges 13a of the respective leg-surrounding side edge portions 13 curve inwardly in the transverse direction of the article 1A from tops 16a, 17a toward bottoms 16b, 17b of the respective leg-holes 16, 17 so that a transverse dimension between the free edges 13a is minimized in the vicinity of the bottoms 16b, 17b of the respective leg-holes 16, 17. In the article 1A, as will be seen in FIG. 3, a transverse dimension of the crotch region 9 is smaller than a transverse dimension of both the front waist region 8 and the rear waist region 10 so as to present a substantially hourglass-like planar shape.

The outer sheet 4 is formed by a composite nonwoven fabric comprising substantially non-stretchable hydrophobic fibrous nonwoven fabric layers 4a, 4b laminated with each other. The panel 5 extends over the crotch region 9 into the front and rear waist regions 8, 10, respectively. The panel 5 comprises a mixture of fluff pulp and super-absorbent polymer particles or a mixture of fluff pulp, super-absorbent polymer particles and a thermoplastic synthetic resin fiber, in both cases, compressed to a given thickness. With consequence, the panel 5 has stiffness higher than those of the top- and backsheets 2, 3 and the outer sheet 4.

In the crotch region 9, first and second folding guides 19, 20 spaced from and opposed to each other in the transverse direction so as to extend in the leg-surrounding direction and a pair of third folding guides 21 spaced from and opposed to each other in the leg-surrounding direction so as to extend in the transverse direction. The crotch region 9 is provided in its transversely middle zone 9a with a panel-free zone 22 in the panel 5. The panel 5 is provided inside its transversely opposite side edges 5c with a pair of fourth folding guides 23 extending in the leg-surrounding direction.

The first folding guide 19 is formed on the left half of the crotch region 9 and curves inwardly in the transverse direction from the free edge 13a of the leg-surrounding side edge portion 13 lying in the vicinity of the top 16a of the left leg-hole 16 toward the transversely middle zone 9a of the crotch region 9. The first folding guide 19 is defined by either side sections 19a respectively extending between the free edge 13a of the left leg-surrounding side edge portion 13 and the transversely middle zone 9a and the middle section 19b lying in the transversely middle zone 9a and extending between the either side sections 19a. The either side sections 19a extend from the free edge 13a of the left leg-surrounding side edge portion 13 to the transversely middle zone 9a of the crotch region 9 so as to get nearer to a center line L bisecting the crotch region 9 in left and right halves. The middle section 19b extends substantially in parallel to the center line L.

The second folding guide 20 is formed on the right half of the crotch region 9 and curves inwardly in the transverse direction from the free edge 13a of the leg-surrounding side edge portion 13 lying in the vicinity of the top 17a of the right leg-hole 17 toward the transversely middle zone 9a of the crotch region 9. The second folding guide 20 is defined by either side sections 20a respectively extending between the free edge 13a of the right leg-surrounding side edge portion 13 and the transversely middle zone 9a and the middle section 20b lying in the transversely middle zone 9a and extending between the either side sections 20a. The either side sections 20a extend from the free edge 13a of the right leg-surrounding side edge portion 13 to the transversely middle zone 9a of the crotch region 9 so as to get nearer to the center line L. The middle section 20b extends substantially in parallel to the center line L. The middle sections 19b, 20b of the first and second folding guides 19, 20 are spaced from each other by a given dimension in the transverse direction with the center line L therebetween.

The third folding guides 21 are provided in the transversely middle zone 9a of the crotch region 9 and extend in the transverse direction between the first and second folding guides 19, 20. More specifically, these third folding guides 21 are formed in the panel-free zone 22 which is, in turn, formed in the panel 5. Instead of forming the third folding guides 21 in the transversely middle zone 9a of the crotch region 9, it is possible to form the third folding guides 21 at the positions in the crotch region 9 put aside toward the front and rear waist regions 8, 10.

The fourth folding guides 23 are provided in the crotch region 9 and respectively extend in the leg-surrounding direction between the third folding guides 21 and the front end 5a of the panel 5 lying in the front waist region 8. These fourth folding guides 23 extend from the third folding guides 21 to the front end 5a of the panel 5 so as to be gradually spaced from the center line L. The fourth folding guides 23 are formed in a panel-free zone 24. It is possible to form the fourth folding guides 23 not only in the crotch region 9 but also in the front waist region 8. It is also possible to form the fourth folding guides 23 in the front waist region 8 alone.

The crotch region 9 has a first region 25 extending between the first folding guide 19 and the free edge 13a of the left leg-surrounding side edge portion 13, a second region 26 extending between the second folding guide 20 and the free edge 13a of the right leg-surrounding side edge portion 13, and a third region 27 extending between the middle zones 19b, 20b of the first and second folding guides 19, 20 and the third folding guide 21.

The first region 25 is folded inward of the article 1A along the first folding guide 19 so as to be tucked toward the inner side of the left leg-hole 16. The second region 26 is folded inward of the article 1A along the second folding guide 20 so as to be tucked toward the inner side of the right leg-hole 17. The third region 27 is folded inward of the article 1A along the third folding guides 21 so as to be tucked toward the waist-hole 15.

In the article 1A, the first–third regions 25, 26, 27 may be folded along the first–third folding guides 19, 20, 21, respectively, to form imaginary folding lines 28, 29, 30 as indicated by dashed lines in FIG. 3. Then the first–third regions 25, 26, 27 may be folded along the imaginary folding lines 28, 29, 30 in conjunction with the folding guides 19, 20, 21. A sub-region 25a of the first region 25 extending between the middle zone 19b of the first folding guide 19 and the imaginary folding line 28 is contoured by a sub-region 25b of the first region 25 defined by the free edge 13a of the left leg-surrounding side edge portion 13, the either side sections 19a and the imaginary folding line 28. A sub-region 26a of the second region 26 extending between the middle zone 20b of the second folding guide 20 and the imaginary folding line 29 is contoured by a sub-region 26b of the second region 25 defined by the free edge 13a of the right leg-surrounding side edge portion 13, the either side sections 20a and the imaginary folding line 29.

In the pad 6, the longitudinally opposite end portions 2a, 3a of the top- and backsheets 2, 3 extending outwardly in the longitudinal direction beyond the front and rear ends 5a, 5b of the panel 5 are overlaid and have respective inner surfaces bonded to each other. The transversely opposite side edge portions 2b, 3b of the top- and backsheets 2, 3 extending outwardly in the transverse direction beyond the transversely opposite side edges 5c are overlaid and have respective inner surfaces bonded to each other. The pad 6 is provided on the outer surface of the topsheet 2 with elastic members 31 secured in a stretched state thereto and extending in the leg-surrounding direction. The elastic members 31 are covered with portions of the topsheet 2 folded back. Specifically, the transversely opposite side edge portions 2b, 3b of the top- and backsheets 2, 3 are folded back in the transverse direction of the article 1A in the front and rear waist regions 8, 10. The side edge portions 2b, 3b of the sheets 2, 3 lying in the front and rear regions 8, 10 are thus collapsed inwardly in the transverse direction of the article 1A and the outer surface of the topsheet 2 facing itself are bonded together.

Though not shown, it is possible to provide the pad 6 outside the respective side edges 5c of the panel 5 with leak-barrier sheets independently of the top- and backsheets 2, 3. In this case, such leak-barrier sheets have fixed side edge portions fixed the article 1A outside the side edges 5c of the panel 5, free side edge portions normally biased to rise above the panel 5 and longitudinally opposite end portions collapsed inwardly in the transverse direction of the article 1A and bonded to the article 1A in the vicinity of transversely opposite side edges 5a, 5b of the panel 5 in such a collapsed state. The free side edge portions are provided with elastic members extending in the leg-surrounding direction and attached thereto in a stretched state. A stock material for the leak-barrier sheets may be selected from the group consisting of a hydrophobic fibrous nonwoven fabric and a composite sheet comprising the hydrophobic fibrous nonwoven fabric and a liquid-impervious plastic film laminated thereupon.

The respective leg-surrounding side edge portions 13 are formed by the transversely opposite side edge portions 2b, 3b of the top- and backsheets 2, 3 and portions of the outer sheet 4 extending outwardly in the transverse direction beyond the transversely opposite side edges 5c of the panel 5. The leg-surrounding side edge portions 13 is provided with elastic members 32 extending in the leg-surrounding direction and secured thereto in a stretched state. The leg-surrounding elastic members 32 are interposed between the nonwoven fabric layers 4a, 4b and secured to these nonwoven fabric layers 4a, 4b. The waist-end portions 11 and the transversely opposite side edge portions 12 are formed by portions of the outer sheet 4 extending outwardly in the longitudinal direction beyond the longitudinally opposite ends 5a, 5b and in the transverse direction beyond the transversely opposite side edges 5c of the panel 5. The waist-end portions 11 are respectively provided with band-like waist-surrounding elastic members 33 extending in the waist-surrounding direction and secured thereto in a stretched state. These waist-surrounding elastic members 33 are interposed between the nonwoven fabric layers 4a, 4b and secured to the nonwoven fabric layers 4a, 4b.

To erect the article 1A in its state shown in FIG. 1 from its state shown in FIG. 3 in the plan view, the article 1A is folded in the crotch region 9 with the pad 6 inside so that the front and rear waist regions 8, 10 may face each other, and then the front and rear waist regions 8, 10 are connected to each other by joining them in the vicinity of the respective side edge portions 12. Finally, the first and second regions 25, 26 are folded along the first and second folding guides 19, 20 so that these regions 25, 26 may be tucked toward the inner side of the left and right leg-holes 16, 17 as indicated by an arrow W1 in FIG. 2. Then the third region 27 is folded along the third folding guides 21 so that the third region 27 maybe tucked inward of the article 1A toward the waist-hole 15.

Figure 4:
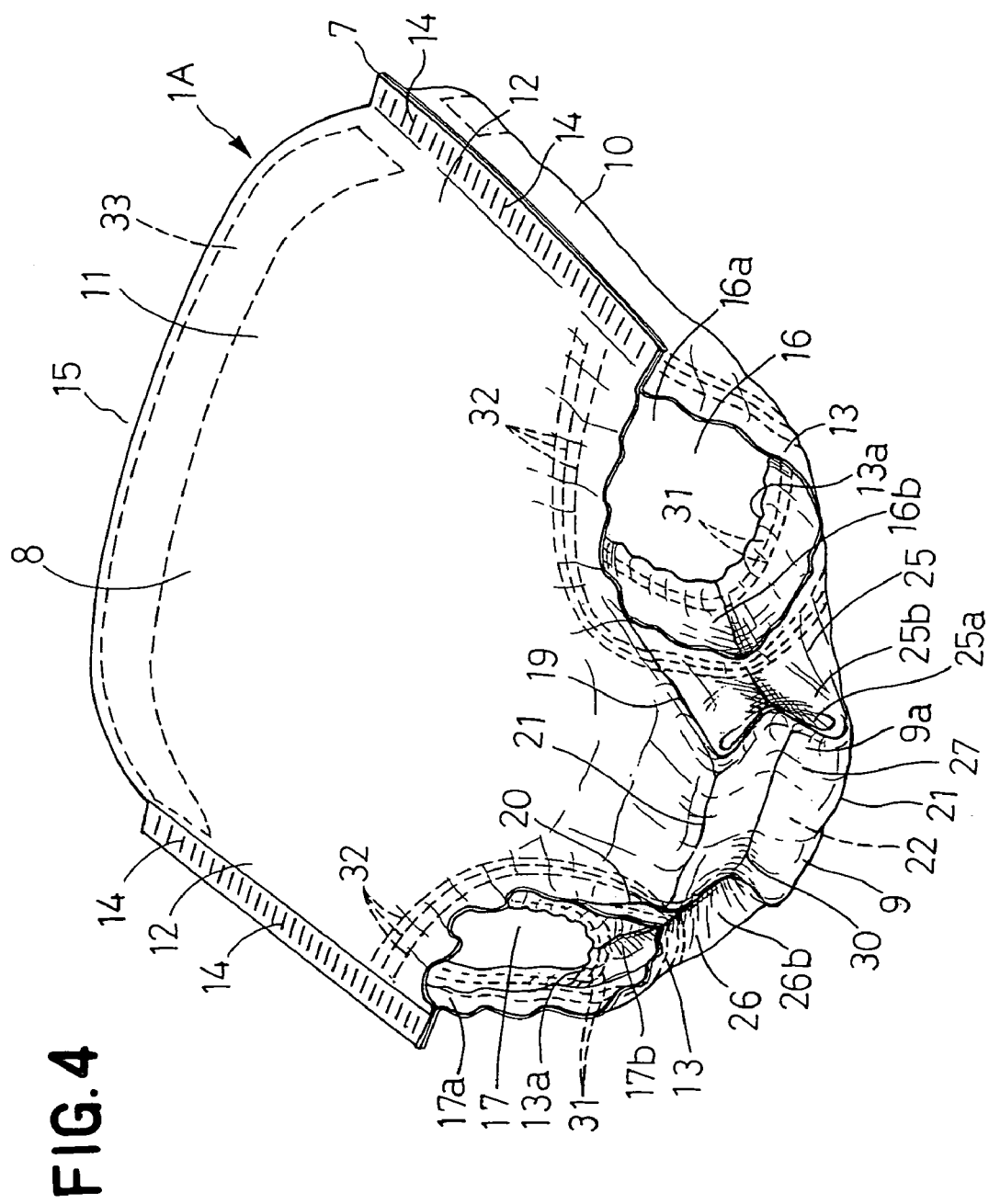
FIG. 4 is a perspective view of the article as viewed from the side of the crotch region.
Figure 5:
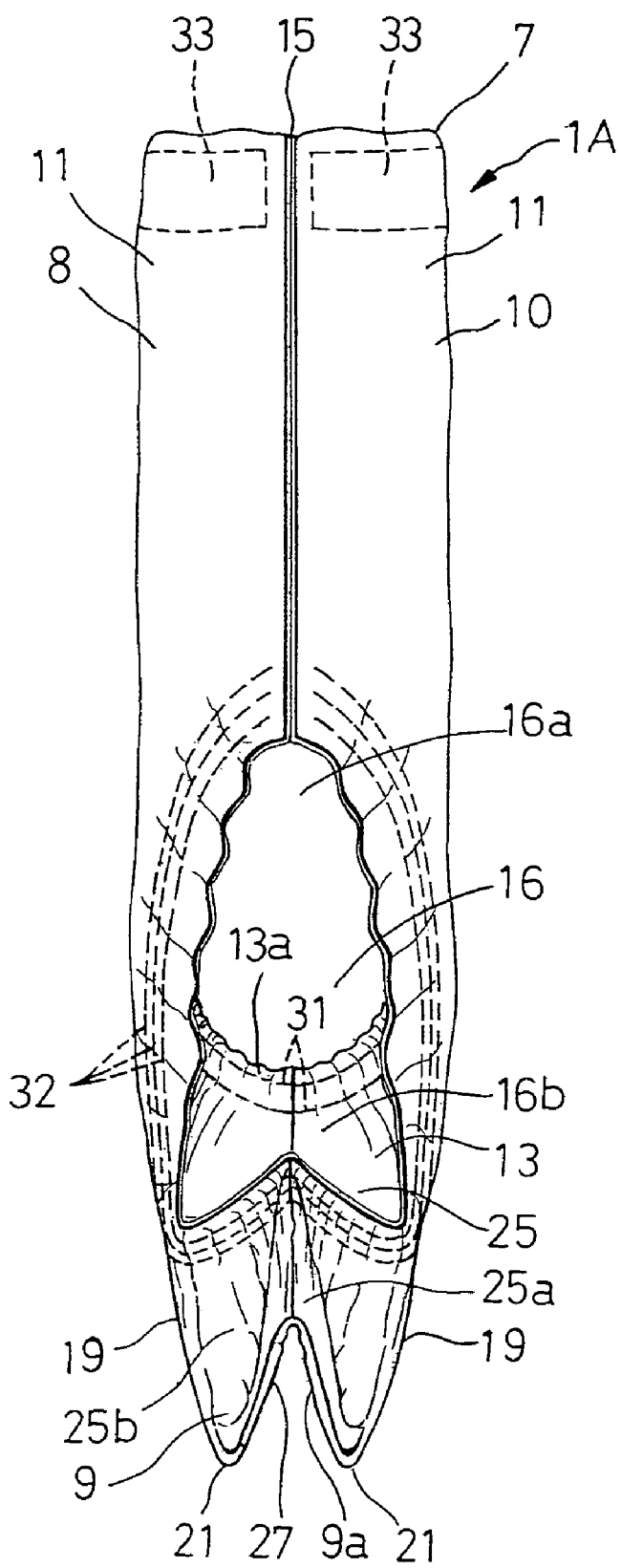
FIG. 5 is a perspective view of the article as viewed from the side of the left leg-hole.
Figure 6:
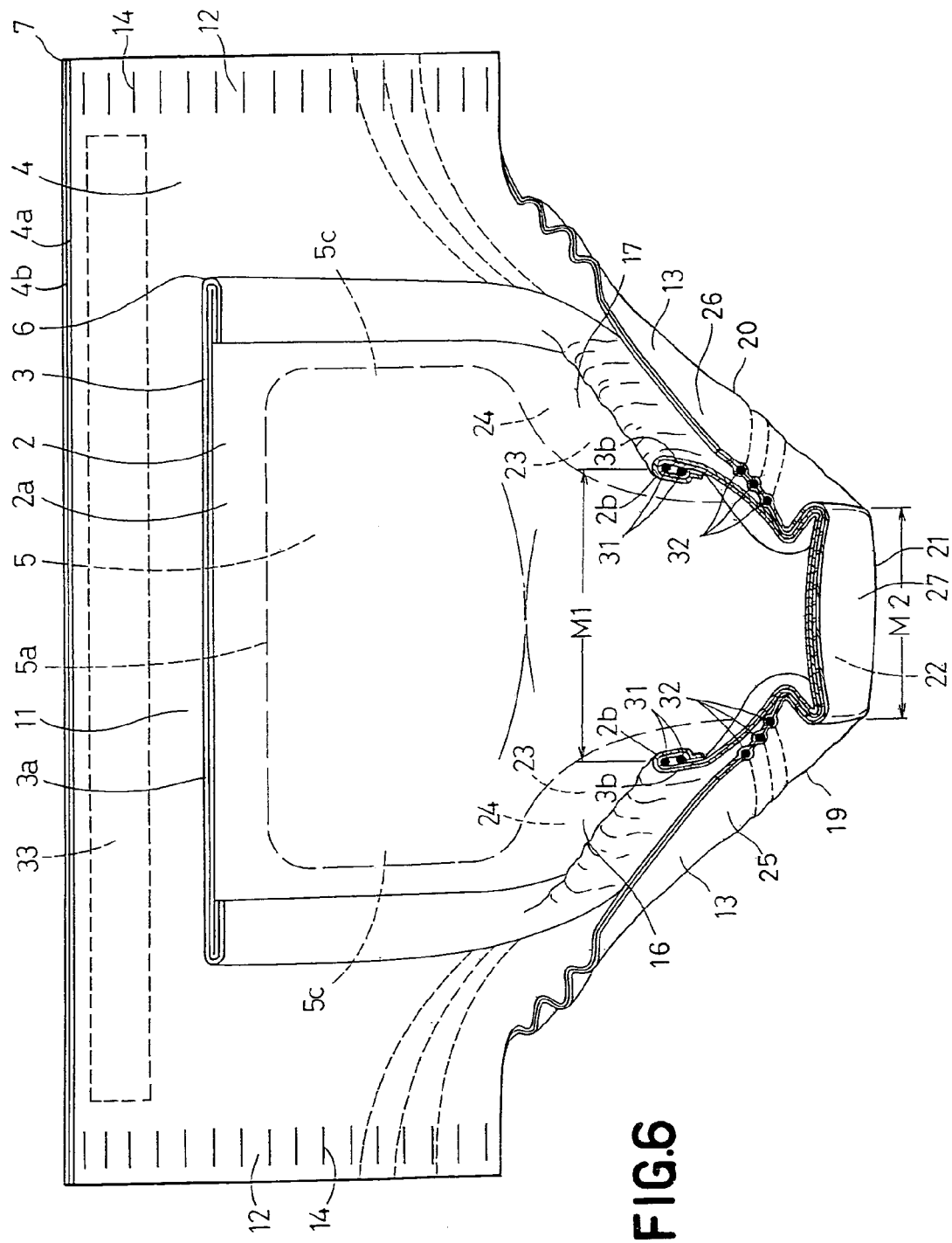
FIG. 6 is a sectional view taken along a line A—A in FIG. 1.
Figure 7:
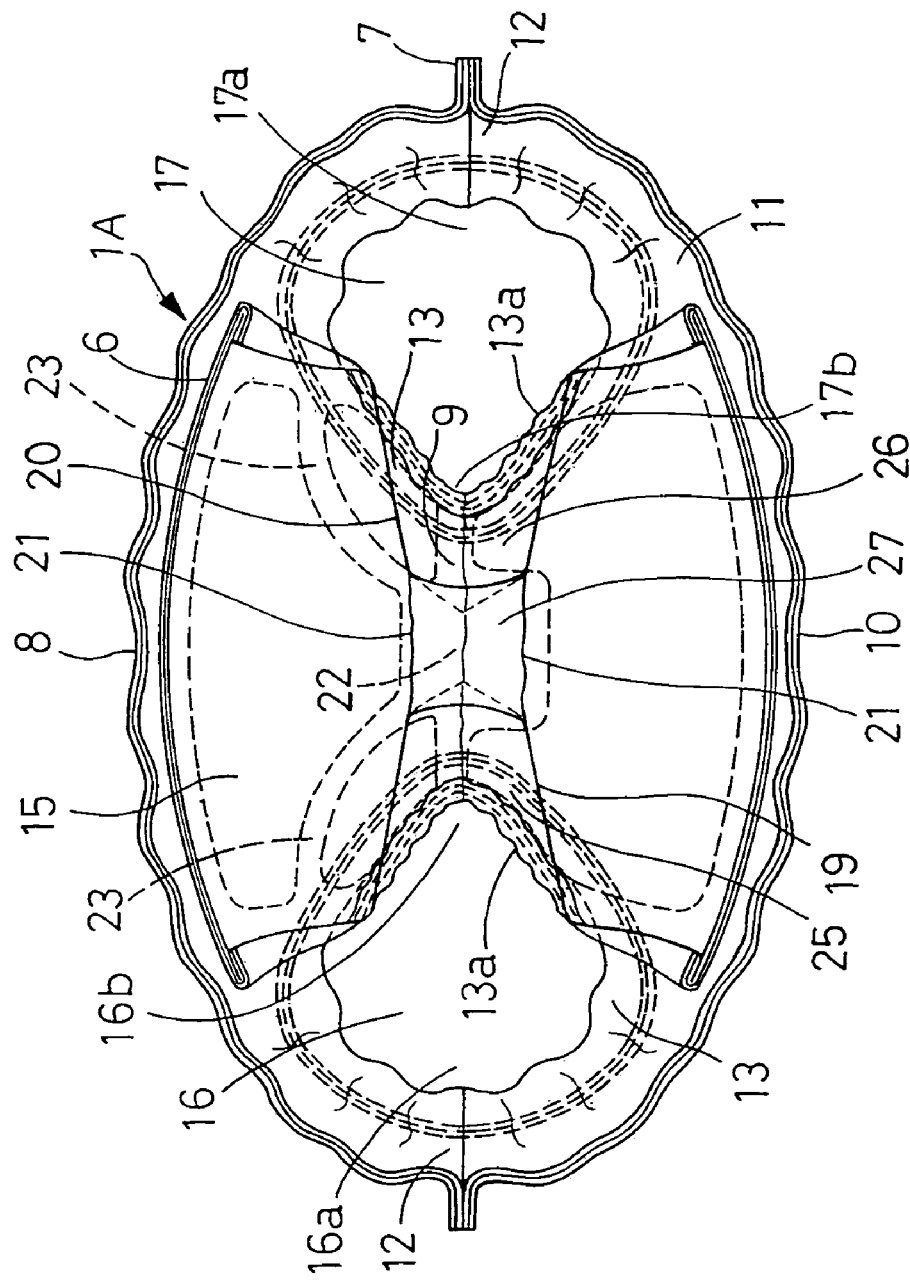
FIG. 7 is a diagram illustrating the article of FIG. 1 with the waist-hole opened, as viewed from above this waist-hole.

FIG. 4 is a perspective view of the article 1A as viewed from the side of the crotch region 9, FIG. 5 is a perspective view of the article 1A as viewed from the side of the left leg-hole 16, FIG. 6 is a sectional view taken along a line A—A in FIG. 1 and FIG. 7 is a diagram illustrating the article 1A of FIG. 1 with the waist-hole 15 opened, as viewed from above this waist-hole 15.

Compared to the state shown in FIG. 2 in which the first, second and third regions 25, 26, 27 are still not tucked, the free edges 13a of the respective leg-surrounding side edge portions 13 have got nearer inwardly to each other in the transverse direction of the article 1A, in other words, the spacing dimension between the free edges 13a of the respective leg-surrounding side edge portions 13 have been further reduced.

With the first and second regions 25, 26 having been tucked, the transverse dimension M2 of the crotch region 9 in the vicinity of the bottoms 16b, 17b of the respective leg-holes 16, 17 is reduced substantially to the minimum transverse dimension M1 between the free edges 13a of the respective leg-surrounding side edge portions 13 and thereby the transverse dimension M2 of the crotch region 9 in the vicinity of the bottoms 16b, 17b of the respective leg-holes 16, 17 can be reduced substantially to the transverse dimension (approximately 3–8 cm) of the wearer's crotch or less.

The portion of the crotch region 9 lying in the vicinity of the bottoms 16b, 17b of the respective leg-holes 16, 17 is fitly put in the wearer's crotch as the article 1A is put on the wearer's body, so the wearer is free from any uncomfortable feeling. Furthermore, there is no possibility that the leg-surrounding side edge portions 13 might be irregularly folded and be formed with a plurality of irregular wrinkles even if the crotch region 9 of the article 1A is squeezed in the wearer's crotch. There is no anxiety, therefore, that the bodily discharge absorbing capacity of the crotch region 9 might be deteriorated and any amount of bodily discharges might leak from the crotch region 9.

In the article 1A having the first and second regions 25, 26 tucked, the minimum spacing dimension M1 between the free edges 13a of the leg-surrounding side edge portions 13 is in a range of 3–9 cm in the vicinity of the bottoms 16b, 17b of the leg-holes 16, 17. If the minimum spacing dimension M1 is less than 3 cm, it would be difficult for the crotch region 9 to receive bodily discharges in the vicinity of the bottoms 16b, 17b of the respective leg-holes 16, 17 and there is an anxiety that a certain amount of bodily discharges might leak beyond the free edges 13a of the respective leg-surrounding side edge portions 13. In addition, the minimum transverse dimension M2 in the vicinity of the bottoms 16b, 17b of the respective leg-holes 16, 17 would be excessively less than the transverse dimension of the wearer's crotch and the crotch region 9 might shift in the wearer's crotch. If the minimum spacing dimension M1 exceeds 9 cm, on the other hand, the crotch region 9 would become too bulky to be fitly received in the wearer's crotch and give the wearer of the article 1A uncomfortable feeling.

In the article 1A, a dimension M3 by which the middle zones 19b, 20b of the first and second folding guides 19, 20 are spaced from each other in the transverse direction is preferably in a range of 3–9 cm. If this spacing dimension M3 is less than 3 cm, the minimum spacing dimension M1 between the free edges 13a of the respective leg-surrounding side edge portions 13 would be less than 3 cm in the vicinity of the bottoms 16b, 17b of the respective leg-holes 16, 17 after the first and second regions 25, 26 have been folded along the first and second folding guides 19, 20. If the spacing dimension M3 exceeds 9 cm, on the other hand, the minimum spacing dimension M1 between the free edges 13a of the respective leg-surrounding side edge portions 13 would exceed 9 cm in the vicinity of the bottoms 16b, 17b of the respective leg-holes 16, 17 even after the first and second regions 25, 26 have been folded along the first and second folding guides 19, 20.

In the article 1A, a dimension M4 by which the third folding guides 21 are spaced from each other in the leg-surrounding direction is preferably in a range of 3–12 cm. If this spacing dimension M4 is less than 3 cm, it would be difficult to tuck the third region 27 along the third folding guides 21. If the spacing dimension M4 exceeds 12 cm, on the other hand, the minimum spacing dimension M3 between the middle zones 19*b*, 20*b* of the first and second folding guides 19, 20 would exceed 9 cm after the third region 27 has been folded along the third folding guides 21. Consequently, the crotch region 9 would become too bulky to be fitly received in the wearer's crotch and give the wearer of the article 1A uncomfortable feeling even after the first and second regions 25, 26 have been folded along the first and second folding guides 19, 20.

It will be seen in FIG. 6 that, in the article 1A, the first and second regions 25, 26 as well as the portions of the panel 5 lying in these regions 25, 26 rise toward the waist-hole 15 as the first and second regions 25, 26 are tucked toward the inner sides of the left and right leg-holes 16, 17. In the article 1A, these regions 25, 26 and the portions of the panel 5 rising in this manner cooperate one with another to form barriers against leakage of bodily discharges and these portions of the panel 5 lying in the first and second regions 25, 26 serve to absorb bodily discharges. In this way, it is not likely that any amount of bodily discharges might leak from the crotch region 9 in the vicinity of the bottoms 16*b*, 17*b* of the respective leg-holes 16, 17.

In the article 1A, the third region 27 tucked toward the waist-hole 15 rises from the bottoms 16*b*, 17*b* of the respective leg-holes 16, 17 toward the waist-hole 15 so as to form a barrier against leakage of bodily discharges. In the article 1A, the third region 27 forming the barrier serves to prevent the amount of excretion discharged onto the front waist region 8 from flowing into the rear waist region 10 and simultaneously to prevent the amount of excretion discharged onto the rear waist region 10 from flowing into the front waist region 8. In the article 1A having its third region 27 tucked, a longitudinal dimension from the waist-end portions 11 to the crotch region 9 can be reduced and thereby the article 1A can be made compact.

In the article 1A, the crotch region 9 is provided in its transversely middle zone 9*a* with the panel-free zone 22 to facilitate the third region 27 to be tucked and thereby to prevent the transversely middle zone 9*a* of the crotch region 9 from becoming bulky. In the transversely middle zone 9*a* of the crotch region 9, the top- and backsheets 2, 3 having stiffness lower than that of the panel 5 come into contact with the wearer's crotch and alleviate uncomfortable feeling possibly experienced by the wearer if the third region 27 which is convex toward the waist-hole 15 comes in direct contact with the wearer's crotch.

As will be best seen in FIG. 7, the waist-hole 15 is aligned with the bottoms 16*b*, 17*b* of the respective leg-holes 16, 17 substantially on straight lines and the bottoms 16*b*, 17*b* of the leg-holes 16, 17 lie ahead of the waist-hole 15 as viewed from above the waist-hole 15. Thus, the article 1A is free from inconvenience such that the wearer's toes and/or heels might get stuck with the side edge portions 13 lying in the vicinity of the bottoms 16*b*, 17*b* of the leg-holes 16, 17 as the wearer's legs are guided through the waist-hole 15 into the respective leg-holes 16, 17 and consequently there is no anxiety that the operation of wearing the article 1A might be retarded.

The transversely opposite side edges 5*b* of the panel 5 lying in the crotch region 9 are folded along the fourth folding guides 23 as the article 1A is put on the wearer's body so that the side edges 5*b* of the panel 5 may be closely placed against inguinal regions of the wearer and thereby any gap may be prevented from being left between the side edges 5*c* of the panel 5 and the inguinal regions of the wearer.

Figure 8:
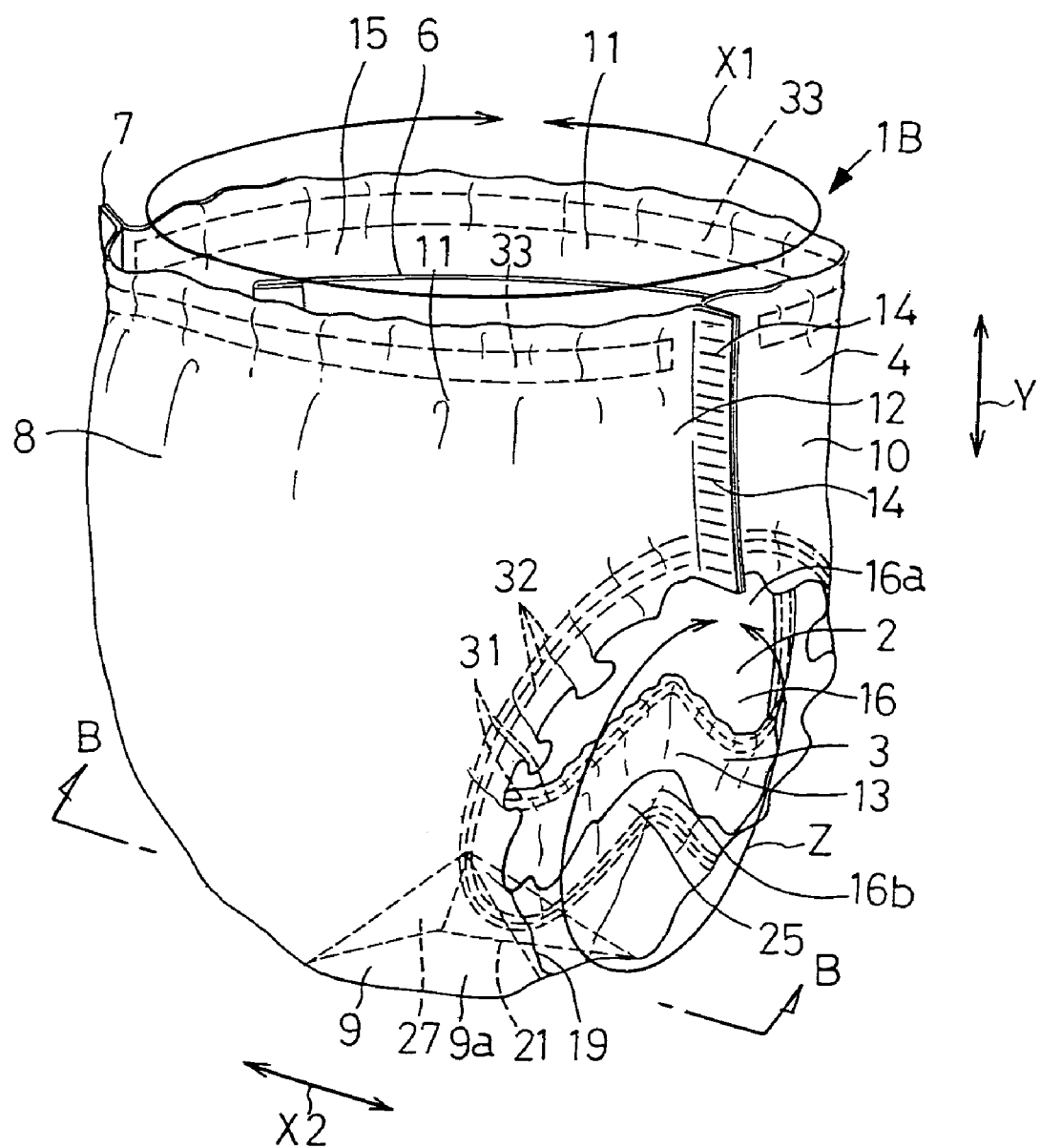
FIG. 8 is a perspective view showing another embodiment of the wearing article according to this invention.
Figure 9:
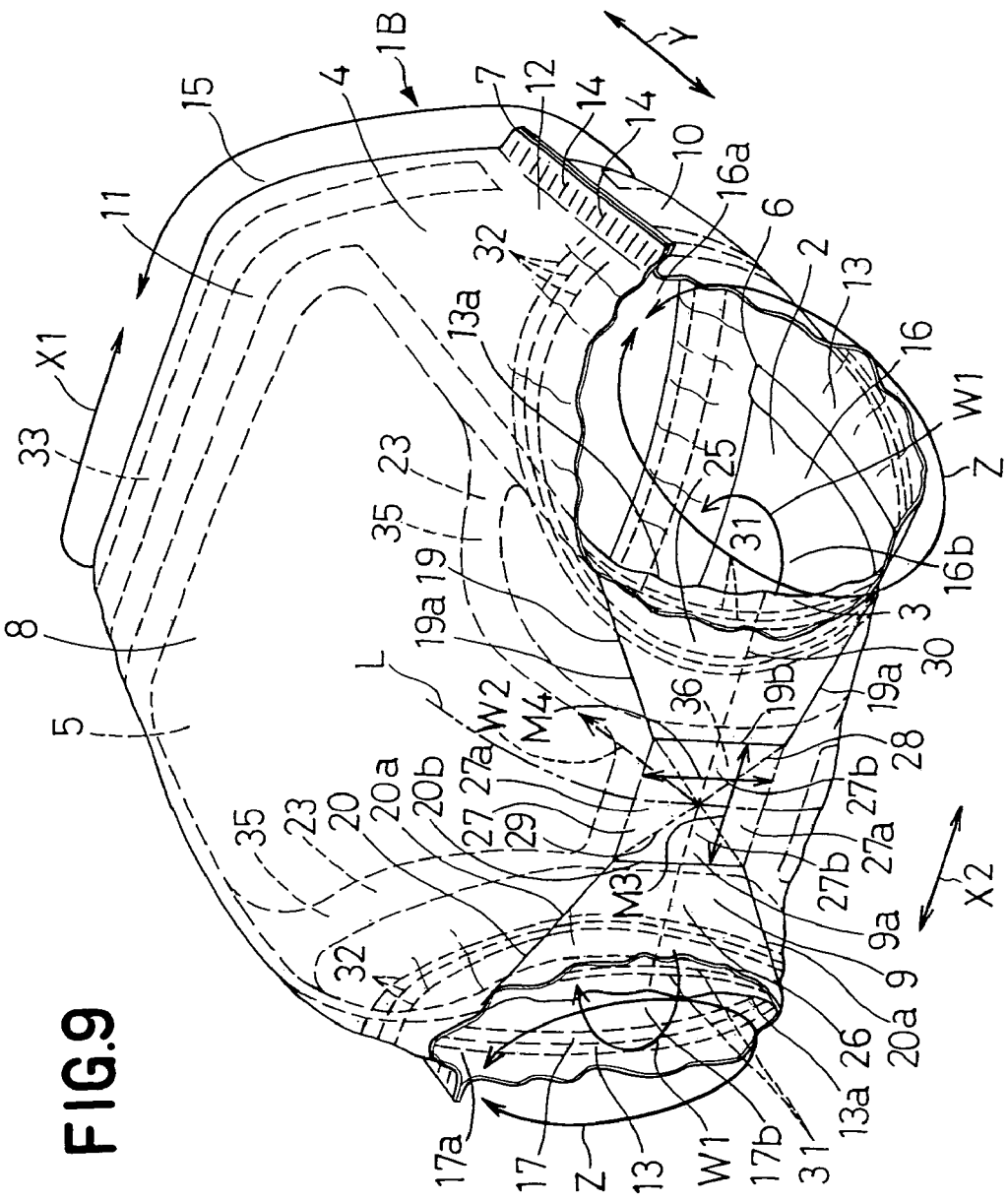
FIG. 9 is a perspective view showing the article prior to tucking of the first–third regions.
Figure 10:
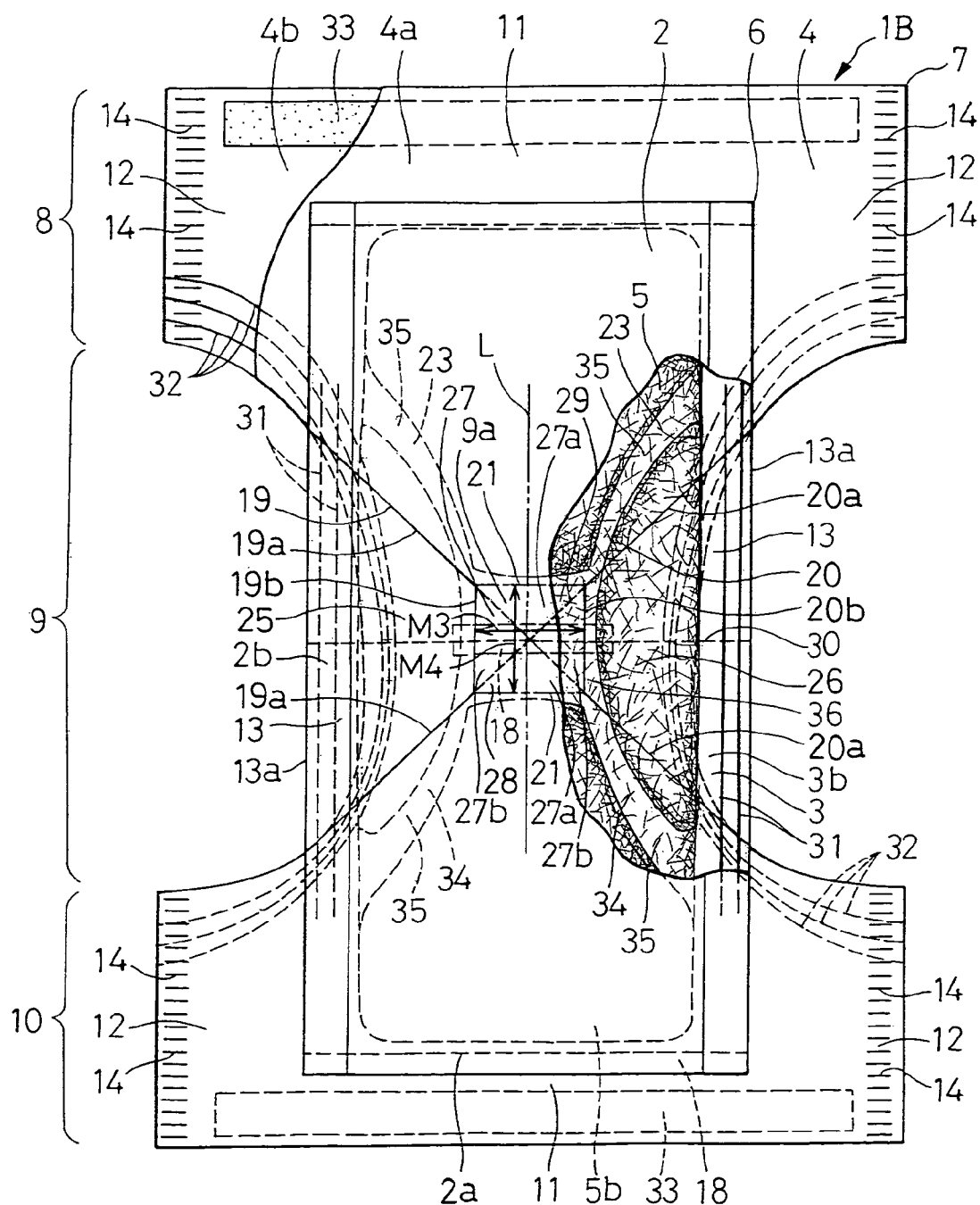
FIG. 10 is a partially cutaway developed plan view showing the article of FIG. 9 with the front and rear waist regions disconnected from each other.

FIG. 8 is a perspective view showing another embodiment 1B of the wearing article according to this invention, FIG. 9 is a perspective view showing this article 1B prior to tucking of the first–third regions 25, 26, 27 and FIG. 10 is a partially cutaway developed plan view showing the article 1B of FIG. 9 with the front and rear waist regions 8, 10 disconnected from each other. In FIGS. 8 and 9, the waist-surrounding direction is indicated by the arrow X1, the transverse direction is indicated by the arrow X2, the longitudinal direction is indicated by the arrow Y and the leg-surrounding direction is indicated by the arrow Z. In FIGS. 9 and 10, first and second folding guides 19, 20 are indicated by solid lines and third folding guides 21 are indicated by dashed lines.

The article 1B is similar to the article 1A of FIG. 1 in that this article 1B also comprises the liquid-pervious topsheet 2 (liquid-pervious sheet) facing the wearer's body, the liquid-impervious backsheet 3 (liquid-impervious sheet) facing away from the wearer's body, the liquid-impervious outer sheet 4 (liquid-impervious sheet) lying outside the backsheet 3 and the liquid-absorbent panel 5 interposed between the top- and backsheets 2, 3 wherein the crotch region 9 has the first-fourth folding guides 19, 20, 21, 23. In the article 1B also, the top- and backsheets 2, 3 cooperate with the panel 5 to define the liquid-absorbent pad 6, and the outer sheet 4 defines pants 7. The article 1B is distinguished from the article 1A of FIG. 1 in the arrangement as will be described.

In the article 1B, the panel 5 is further provided inside the side edges 5*c* with a pair of fifth folding guides 34 extending in the leg-surrounding direction. These fifth folding guides 34 are formed in the crotch region 9 and extend in the leg-surrounding direction between the respective third folding guides 21 and the rear end 5*b* of the panel 5 lying in the rear waist region 10. The fifth folding guides 34 extend from the respective third folding guides 21 toward the rear end 5*b* of the panel 5 so as to be gradually spaced from the center line L. It is possible to form the fifth folding guides 34 not only in the crotch region 9 but also in the rear waist region 10 or to form them in the rear waist region 10 alone.

The fourth folding guides 23 as well as the fifth folding guides 34 are formed by low stiffness zones 35 having a stiffness lower in these folding guides 23, 34 than in the other zone of the panel 5. The crotch region 9 is formed in its transversely middle zone 9*a* with a low stiffness zone 36 in which the panel 5 has a stiffness lower than in the other zone.

In these low stiffness zones 35, 36, at least one of fluff pulp and thermoplastic synthetic resin fibers forming together the panel 5 has a basis weight per unit volume lower than a basis weight per unit volume of the panel 5 except for these low stiffness zones 35, 36. The panel 5 has a thickness dimension smaller in these low stiffness zones 35, 36 than in the other zone of the panel 5.

The first region 25 is folded inward of the article 1B along the first folding guide 19 so as to be tucked toward the inner side of the left leg-hole 16. The second region 26 is folded inward of the article 1B along the second folding guide 20 so as to be tucked toward the inner side of the right leg-hole 17. The third region 27 is folded inward of the article 1B along the third folding guides 21 so as to be tucked toward the waist-hole 15.

In the article 1B, the first–third regions 25, 26, 27 may be folded along the first–third folding guides 19, 20, 21, respectively, to form imaginary folding lines 28, 29, 30 as indicated by dashed lines. Then the first–third regions 25, 26, 27 may be folded along these imaginary folding lines 28, 29, 30 in conjunction with the folding guides 19, 20, 21. Sub-regions 27*b* of the third region 27 extending between the middle zones 19b, 20b of the first and second folding guides 19, 20 and the imaginary folding lines 28, 29 are contoured by sub-regions 27a of the third region 27 extending between the third folding guides 21 and the imaginary folding lines 28, 29.

To erect the article 1B in its state shown in FIG. 8 from its state shown in FIG. 10 in the plan view, the article 1B is folded in the crotch region 9 with the pad 6 inside so that the front and rear waist regions 8, 10 may face each other, and then the front and rear waist regions 8, 10 are connected to each other by joining them along the respective side edge portions 12. Finally, the first and second regions 25, 26 are folded along the first and second folding guides 19, 20 so that these regions 25, 26 may be tucked toward the inner side of the left and right leg-holes 16, 17 as indicated by the arrow W1 in FIG. 9. Then the third region 27 is folded along the third folding guides 21 so that the third region 27 may be tucked inward of the article 1B toward the waist-hole 15 as indicated by the arrow W2 in FIG. 9.

Figure 11:
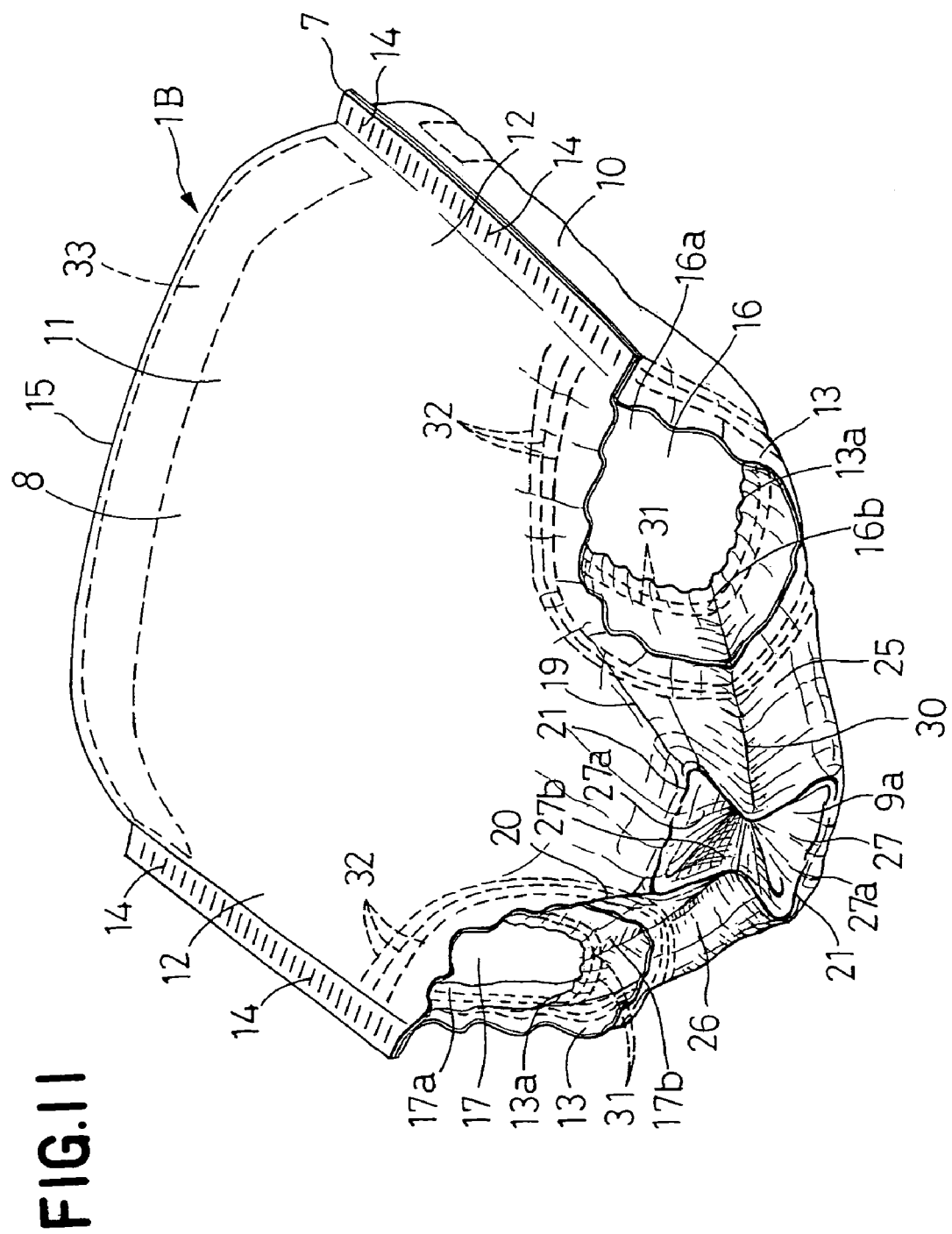
FIG. 11 is a perspective view of the article as viewed from the side of the crotch region.
Figure 12:
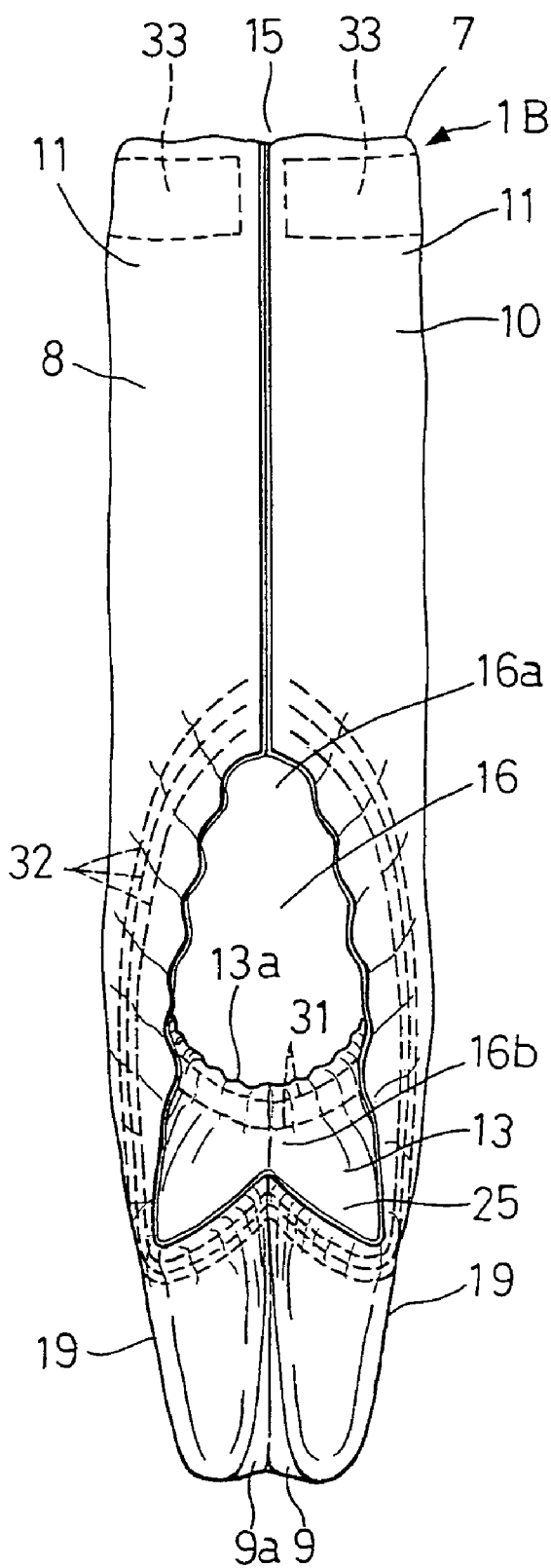
FIG. 12 is a perspective view of the article as viewed from the side of the left leg-hole.
Figure 13:
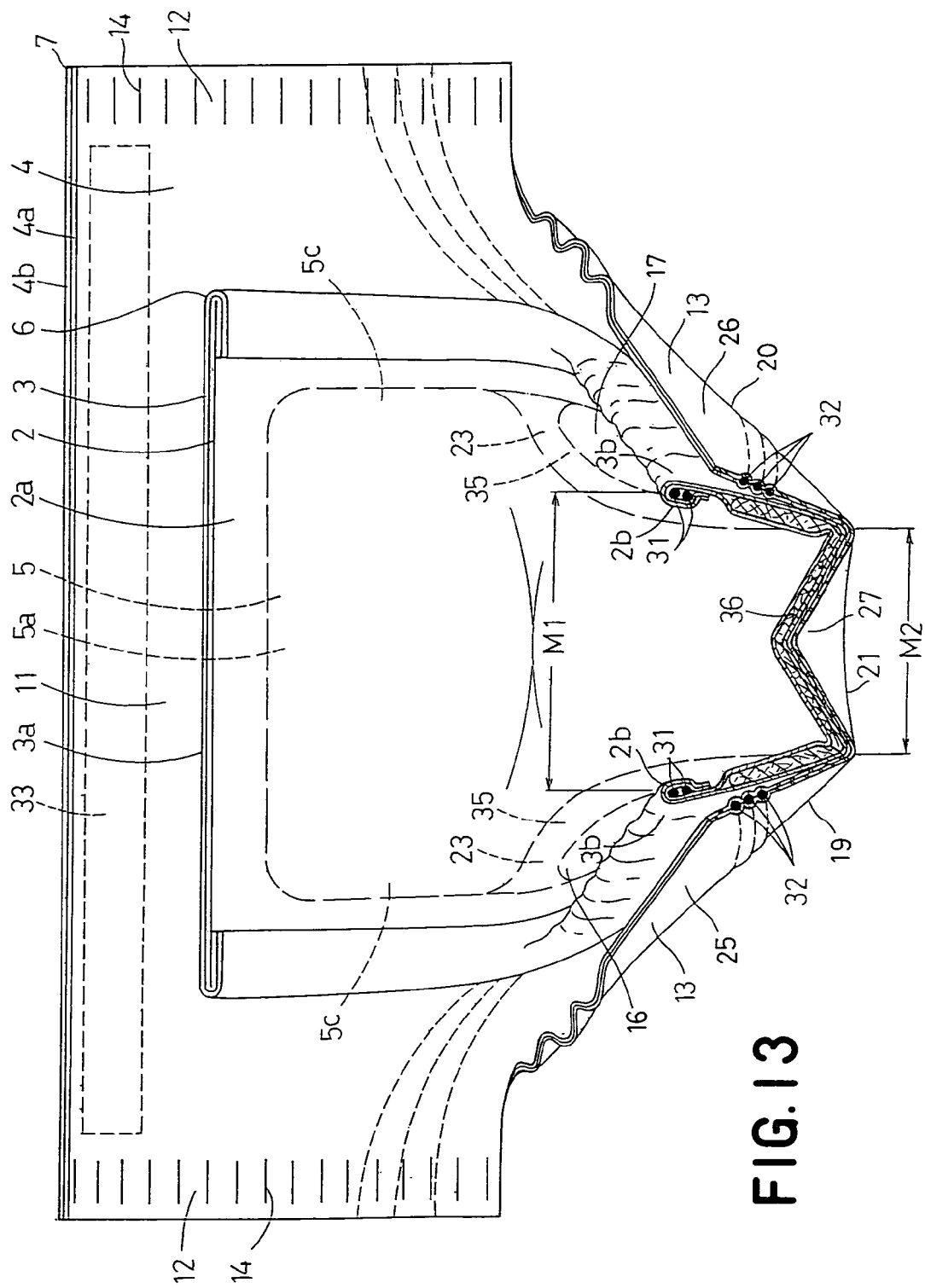
FIG. 13 is a sectional view taken along a line B—B in FIG. 8.
Figure 14:
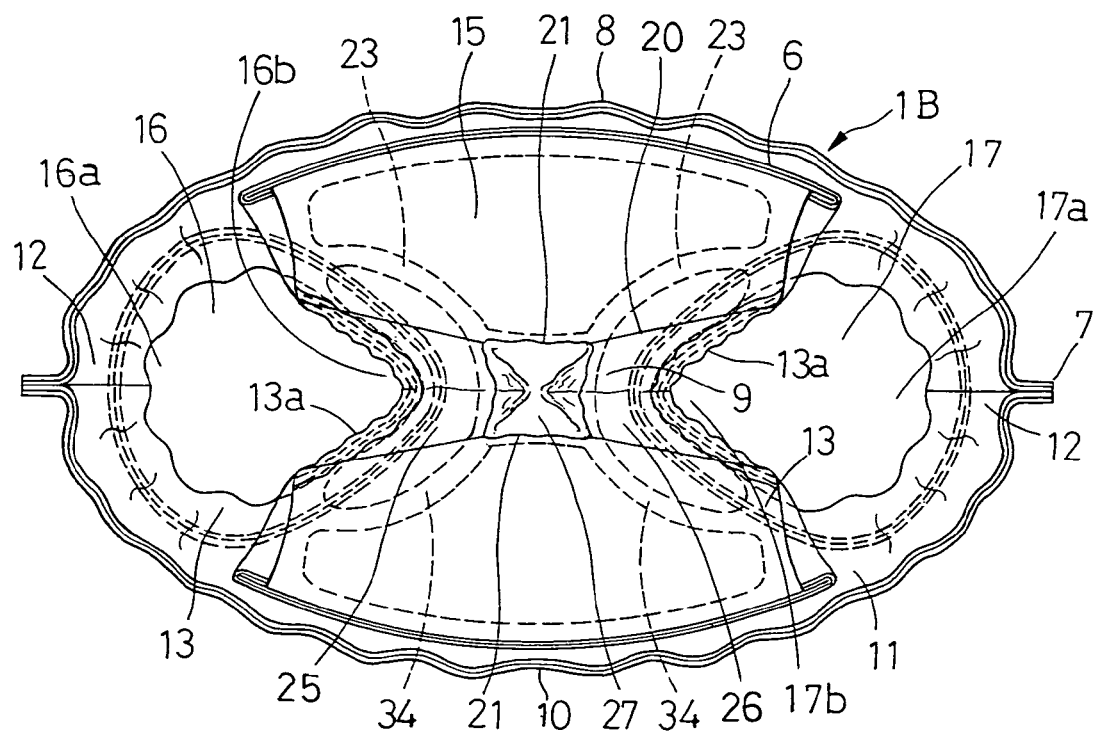
FIG. 14 is a diagram illustrating the article of FIG. 8 with the waist-hole opened, as viewed from above the waist-hole.

FIG. 11 is a perspective view of the article 1B as viewed from the side of the crotch region 9, FIG. 12 is a perspective view of the article 1B as viewed from the side of the left leg-hole 16, FIG. 13 is a sectional view taken along a line B—B in FIG. 8 and FIG. 14 is a diagram illustrating the article 1B of FIG. 8 with the waist-hole 15 opened, as viewed from above this waist-hole 15.

Compared to the state shown in FIG. 9 in which the first, second and third regions 25, 26, 27 are still not tucked, at the bottoms 16b, 17b of the leg-holes 16, 17, the free edges 13a of the respective leg-surrounding side edge portions 13 have got nearer inwardly to each other in the transverse direction of the article 1B, in other words, the spacing dimension of the free edges 13a of the respective leg-surrounding side edge portions 13 have been further reduced.

In this way, the transverse dimension M2 of the crotch region 9 in the vicinity of the bottoms 16b, 17b of the respective leg-holes 16, 17 can be reduced substantially to the minimum transverse dimension M1 between the free edges 13a of the respective leg-surrounding side edge portions 13 and thereby the transverse dimension M2 of the crotch region 9 in the vicinity of the bottoms 16b, 17b of the respective leg-holes 16, 17 can be reduced substantially to the transverse dimension of the wearer's crotch or less. In the article 1B, the portion of the crotch region 9 lying in the vicinity of the bottoms 16b, 17b of the respective leg-holes 16, 17 is fitly put in the wearer's crotch as the article 1B is put on the wearer's body, so the wearer is free from any uncomfortable feeling. Furthermore, there is no possibility that the leg-surrounding side edge portions 13 might be irregularly folded and be formed with a plurality of irregular wrinkles even if the crotch region 9 of the article 1B is squeezed in the wearer's crotch. There is no anxiety, therefore, that the bodily discharge absorbing capacity of the crotch region 9 might be deteriorated and any amount of bodily discharges might leak from the crotch region 9.

In the case of the article 1B, the first and second regions 25, 26 rising toward the waist-hole 15 cooperate with the portions of the panel 5 lying in these regions 25, 26 to form barriers against leakage of bodily discharges and the portions of the panel 5 lying in the transversely middle zone 9a of the crotch region 9 as well as lying in the first and second regions 25, 26 serve together to absorb bodily discharges. In this way, there is no possibility that any amount of bodily discharges might leak from the crotch region 9 in the vicinity of the bottoms 16b, 17b of the leg-holes 16, 17. The article 1B is formed in the transversely middle zone 9a of the crotch region 9 with the low stiffness zone 36 of the panel 5, so the crotch region 9 is capable of absorbing much more amount of bodily discharges than the crotch region 9 in the article 1A of FIG. 1 provided in the transversely middle zone 9a with the panel-free zone 22.

In the article 1B, the third region 27 tucked from the bottoms 16b, 17b of the leg-holes 16, 17 toward the waist-hole 15 so that the third region 27 may define barriers which are convex toward the waist-hole 15 so as to prevent bodily discharges from leaking. The third region 27 forming the barrier in this manner is effective to prevent the amount of excretion discharged onto the front waist region 8 from flowing into the rear waist region 10 and simultaneously to prevent the amount of excretion discharged onto the rear waist region 10 from flowing into the front waist region 8. In the article 1B having its third region 27 tucked toward the waist-hole 15, a longitudinal dimension from the waist-end portions 11 to the crotch region 9 can be reduced and thereby the article 1B can be made compact. In the article 1B, the crotch region 9 is provided in its transversely middle zone 9a with a low stiffness zone 36 adapted to come in contact with the wearer's crotch and to alleviate uncomfortable feeling possibly experienced by the wearer if the third region 27 which is convex toward the waist-hole 15 comes in direct contact with the wearer's crotch.

As will be best seen in FIG. 14, the waist-hole 15 is aligned with the bottoms 16b, 17b of the respective leg-holes 16, 17 substantially on straight lines and the bottoms 16b, 17b of the leg-holes 16, 17 lie ahead of the waist-hole 15 as viewed from above the waist-hole 15. Thus, the article 1B is free from inconvenience such that the wearer's toes and/or heels might get stuck with the side edge portions 13 lying in the vicinity of the bottoms 16b, 17b of the leg-holes 16, 17 as the wearer's legs are guided through the waist-hole 15 into the respective leg-holes 16, 17 and consequently there is no anxiety that the operation of wearing the article 1B might be retarded.

The transversely opposite side edges 5c of the panel 5 are folded along the fourth and fifth folding guides 23, 34 as the article 1B is put on the wearer's body so that the side edges 5c of the panel 5 may be closely placed against inguinal regions of the wearer and thereby any gap may be prevented from being left between the side edges 5c of the panel 5 and the inguinal regions of the wearer.

In the article 1B, the minimum spacing dimension M1 between the free edges 13a of the leg-surrounding side edge portions 13 is in the range of 3–9 cm in the vicinity of the bottoms 16b, 17b of the respective leg-holes 16, 17. In the article 1B, the dimension M3 by which the middle zones 19b, 20b of the first and second folding guides 19, 20 are spaced from each other in the transverse direction is preferably in the range of 3–9 cm. In the article 1B, the dimension M4 by which the third folding guides 21 are spaced from each other in the leg-surrounding direction is preferably in a range of 3–12 cm.

In the article 1A of FIG. 1, it is possible without departing the scope of this invention to form the fifth folding guides 34 in the crotch region 9 and/or to define the fourth folding guides 23 not in the panel-free zone 22 of the panel 5 but by the low stiffness zone 35 of the panel 5. In the article 1B of FIG. 8, it is possible without departing from the scope of this invention to eliminate at least one of the respective pairs of fourth and fifth folding guides 23, 34 or to define these pairs of fourth and fifth folding guides 23, 34 by the panel-free zone 22 of the panel 5. Both in the article 1A and the article 1B, it is possible also without departing from the scope of this invention to eliminate the fourth and fifth folding guides 23, 34 and/or to eliminate both the panel-free zone 22 of the panel 5 and the low stiffness zone 36 from the transversely middle zone 9a of the crotch region 9.

In both the article 1A and the article 1B, on the purpose of reliably retaining these first–third regions 25, 26, 27 in respectively tucked states thereof, the outer surface of the tucked outer sheet 4 lying in the first and second regions 25, 26 is preferably attached to itself after the first–third regions 25, 26, 27 have been tucked. It is also possible that the outer surface of the tucked outer sheet 4 lying in the third region 27.

A stock material for the topsheet 2 may be selected from the group consisting of a hydrophilic fibrous nonwoven fabric, a hydrophobic fibrous nonwoven fabric having a plurality of pores and a plastic film having a plurality of fine pores. A stock material for the backsheet 3 may be selected from the group consisting of a hydrophobic fibrous nonwoven fabric, a breathable but liquid-impervious plastic film, a composite nonwoven fabric comprising two or more hydrophobic fibrous nonwoven fabric layers laminated one with another and a composite sheet comprising a hydrophobic fibrous nonwoven fabric and a breathable but liquid-impervious plastic film laminated with each other. A stock material for the outer sheet 4 may be selected from the group consisting of a hydrophobic fibrous nonwoven fabric, a breathable but liquid-impervious plastic film and a composite sheet comprising a hydrophobic fibrous nonwoven fabric and a breathable but liquid-impervious plastic film laminated with each other. It is also possible to use, as a stock material for the backsheet 3 and the outer sheet 4, a composite nonwoven fabric comprising a melt blown fibrous nonwoven fabric having a high water-resistance and two layers of spun bond fibrous nonwoven fabric each having a high strength and a high flexibility sandwiching the melt blown fibrous nonwoven fabric.

The type of nonwoven fabric to be used may be selected from the group consisting of spun lace-, needle punch-, melt blown-thermal bond-, spun bond-, chemical bond- and air-through-types. Component fibers of the nonwoven fabric may be selected from the group consisting of polyolefine-, polyester- and polyamide-based fibers, and core-sheath type or side-by-side type conjugated fiber of polyethylene/polypropylene or polyethylene/polyester.

It is also possible to use, as a stock material for the outer sheet 4, any one of a stretchable hydrophobic fibrous nonwoven fabric, a stretchable liquid-impervious plastic film, a composite nonwoven fabric comprising two or more layers of stretchable composite nonwoven fabric laminated one with another and a composite sheet comprising a stretchable hydrophobic fibrous nonwoven fabric and a stretchable liquid-impervious plastic film laminated with each other.

It is possible to use melt blown or spun bond nonwoven fabrics as the stretchable nonwoven fabric. It is possible to use, as a component fiber of the stretchable nonwoven fabric, a stretchable fiber obtained by melt spinning thermoplastic elastomer. It is possible to use, as a stock material for the outer sheet 4, a composite nonwoven fabric comprising a stretchable fibrous nonwoven fabric of thermoplastic elastomeric resin fiber and a fibrous nonwoven fabric of crimped fibers obtained by melt spinning thermoplastic synthetic resin selected from the group consisting of polypropylene, polyethylene and polyester and laminated on at least one surface of the stretchable fibrous nonwoven fabric of thermoplastic elastomeric resin.

Preferably, the panel 5 is entirely covered with and bonded to a tissue paper in order to prevent the panel 5 from getting out of shapes and/or to retain the polymer particles within the panel 5. The polymer particles may be selected from the group consisting of a starch-based polymer, a cellulose-based polymer and a synthetic polymer.

To join the top- and backsheets 2, 3 to each other, to secure the panel 5 to the top- and backsheets 2, 3 and to secure the elastic members 31, 32, 33 to the top- and backsheets 2, 3 and the outer sheet 4, hot melt adhesives or heat-sealing techniques such as a heat-sealing or an ultrasonic sealing may be employed.

The pants-type disposable wearing article according to this invention has the advantageous effects that the first and second regions are tucked along the first and second folding guides toward the inside of the leg-holes and the third region is tucked along the third folding guides toward the waist-hole so that the free edges of the respective leg-surrounding side edge portions get nearer inwardly to each other in the transverse direction of the article. Consequently, the spacing dimension between the free edges of the respective leg-surrounding side edge portions get nearer inwardly to each other in the vicinity of the bottoms of the respective leg-holes is reduced with respect to the state before the leg-surrounding side edge portions are tucked.

In the article according to this invention, the waist-hole is aligned with the bottoms of the respective leg-holes substantially on straight lines and the bottoms of the leg-holes lie ahead of the waist-hole, so the article is free from inconvenience such that the wearer's toes and/or heels might get stuck with the side edge portions lying in the vicinity of the bottoms of the leg-holes as the wearer's legs are guided through the waist-hole into the respective leg-holes and consequently there is no anxiety that the operation of wearing the article might be retarded. In the article having its third region tucked inward of the article toward the waist-hole, a longitudinal dimension from the waist-end portions to the crotch region can be reduced and thereby the article can be made compact.

In the article according to this invention, a transverse dimension of the portion of the crotch region lying in the vicinity of the bottoms of the respective leg-holes is equal to or smaller than a transverse dimension of the wearer's crotch so as to be fitly put in the wearer's crotch as the article is put on the wearer's body, so the wearer is free from any uncomfortable feeling. Furthermore, there is no possibility that the leg-surrounding side edge portions might be irregularly folded and be formed with a plurality of irregular wrinkles even if the crotch region of the article is squeezed in the wearer's crotch. There is no anxiety, therefore, that the bodily discharge absorbing capacity of the crotch region might be deteriorated and any amount of bodily discharges might leak from the crotch region.

In the article, the first and second regions lying in the vicinity of the bottoms of the respective leg-holes and rising above the panel form the barriers against leakage of bodily discharges. The barriers effectively eliminate the possibility that any amount of bodily discharges might leak from the crotch region in the vicinity of the bottoms of the respective leg-holes. The third region becoming convex toward the waist-hole also forms the barrier adapted to prevent the amount of excretion discharged onto the front waist region from flowing to the rear waist region and the amount of excretion discharged onto the rear waist region from flowing to the front waist region.

In the article formed in the transversely middle zone of the crotch region with the panel-free zone or the low stiffness panel zone, the crotch region has a stiffness in its transversely middle zone lower than the other zone of the crotch region. Such a unique feature is effective to alleviate uncomfortable feeling possibly experienced by the wearer if the third region which is convex toward the waist-hole comes in direct contact with the wearer's crotch region.

In the article having the fourth and fifth folding guides extending inside the transversely opposite side edges of the panel in the waist-surrounding direction, the transversely opposite side edges of the panel are folded along the fourth and fifth folding guides as the article is put on the wearer's body so that the side edges of the panel may be closely placed against inguinal regions of the wearer and thereby any gap may be prevented from being left between the side edges of the panel and the inguinal regions of the wearer.

What is claimed is:

1. A pants-type disposable wearing article having front and rear waist regions opposed to each other and a crotch region extending between said waist regions, said article comprising a liquid-pervious sheet, a liquid-impervious sheet and a liquid-absorbent panel interposed between said sheets and extending over said crotch region into said front and rear waist regions so as to define a waist-hole enclosed by waist ends extending in a waist-surrounding direction and left and right leg-holes respectively enclosed by leg-surrounding side edge portions extending in a leg-surrounding direction, said article further comprising:
    a first folding guide extending in left half of said crotch region from a free edge of said leg-surrounding side edge portion lying in a vicinity of a top of said left leg-hole so as to define a convexity toward a transversely middle zone of said crotch region, a second folding guide extending in right half of said crotch region from a free edge of said leg-surrounding side edge portion lying in a vicinity of a top of said right leg-hole so as to define a convexity toward a transversely middle zone of said crotch region and a pair of third folding guides spaced from and opposed to each other in said leg-surrounding direction and transversely extending between said first and second folding guides;
    a first region extending between said first folding guide and said free edge of said leg-surrounding side edge portion, a second region extending between said second folding guide and said free edge of said leg-surrounding side edge portion and a third region contoured by said first and second folding guides and said third folding guides in said crotch region; and
    said first region and said second region folded along said first folding guide and said second folding guide to be tucked toward inner sides of said left and right leg-holes and said third region is folded along said third folding guides to be tucked inwardly of said article toward said waist-hole.

2. The wearing article according to claim 1, wherein said third folding guides are formed in said transversely middle zone of said crotch region.

3. The wearing article according to claim 1, wherein said crotch region is formed in said transversely middle zone with a low stiffness zone so that said panel has a stiffness lower in said low stiffness zone than in other zone of said panel.

4. The wearing article according to claim 1, wherein said crotch region is formed in said transversely middle zone with a panel-free zone.

5. The wearing article according to claim 1, wherein said free edges of said leg-surrounding side edge portions curve inwardly from said tops to bottoms of said leg-holes so that a transverse dimension between said free edges of said side edges is minimized at said bottoms of said leg-holes.

6. The wearing article according to claim 1, wherein a minimum spacing dimension between said free edges of said leg-surrounding side edge portions at said bottoms of said leg-holes is in a range of 3–9 cm after said first and second regions have been tucked.

7. The wearing article according to claim 1, wherein said third region is free of absorbent material of said panel.

8. The wearing article according to claim 1, wherein said third region is a low stiffness zone in which said panel has a stiffness lower than in other zones of said panel.

9. The wearing article according to claim 1, wherein said third region, which is tucked inwardly of said article and toward said waist-hole, defines a concave bottom of said article.

10. The wearing article according to claim 1, wherein said third region, which is tucked inwardly of said article and toward said waist-hole, is further folded along two auxiliary folding guides which extend diagonally of said third region; the folded and tucked third region having an apex pointed toward said waist hole.

11. A pants-type disposable wearing article, comprising:
    front and rear waist regions opposed to each other and a crotch region extending in a longitudinal direction of said article between said waist regions;
    a liquid-pervious sheet, a liquid-impervious sheet and a liquid-absorbent panel interposed between said sheets and extending over said crotch region into said front and rear waist regions;
    a waist-hole, and left and right leg-holes;
    a first folding guide comprising two sections extending from a transversely middle zone of said crotch region toward the front and rear waist regions, respectively, and up to an edge of the left leg-hole;
    a second folding guide comprising two sections extending from the transversely middle zone of said crotch region toward the front and rear waist regions, respectively, and up to an edge of the right leg-hole;
    a pair of third folding guides spaced from each other in said longitudinal direction and transversely extending between said first and second folding guides;
    a first region defined between said first folding guide and the edge of said left leg-hole;
    a second region defined between said second folding guide and the edge of said right leg-hole;
    a third region contoured by said first, second and third folding guides in said crotch region;
    said article being folded along said, first and second folding guides, and said first and second regions being tucked inwardly of said left and right leg-holes, respectively;
    said article being further folded along said third folding guides, and the third region being tucked inwardly of said article and toward said waist-hole; and
    a pair of fourth folding guides located inwardly of transversely opposite side edges of said panel and extending between said third folding guides and an end of said panel lying in one of said front and rear waist regions;
    wherein said fourth folding guides are defined by low stiffness zones in which said panel has a stiffness lower than in other zones of said panel.

12. The wearing article according to claim 11, wherein said article further includes a pair of fifth folding guides located inwardly of said transversely opposite side edges of said panel and extending between said third folding guides and an opposite end of said panel lying in the other one of said front and rear waist regions; and said fifth folding guides are defined by said low stiffness zones.

13. A pants-type disposable wearing article, comprising:
front and rear waist regions opposed to each other and a crotch region extending in a longitudinal direction of said article between said waist regions;
a panel comprising a liquid-pervious sheet, a liquid-impervious sheet and a liquid-absorbent core interposed between said sheets, said panel extending over said crotch region into said front and rear waist regions;
a waist-hole, and left and right leg-holes;
a first folding guide comprising two sections extending from a transversely middle zone of said crotch region toward the front and rear waist regions, respectively, and up to a peripheral edge of the left leg-hole;
a second folding guide comprising two sections extending from the transversely middle zone of said crotch region toward the front and rear waist regions, respectively, and up to a peripheral edge of the right leg-hole;
a pair of third folding, guides spaced from each other in said longitudinal direction and transversely extending between said first and second folding guides;
a first region defined between said first folding guide and the edge of said left leg-hole;
a second region defined between said second folding guide and the edge of said right leg-hole;
a third region contoured by said first, second and third folding guides in said crotch region;
said article being folded along said first and second folding guides, and said first and second regions being tucked inwardly of said article and toward each other; and
said article being further folded along said third folding guides, and the third region being tucked inwardly of said article and toward said waist-hole;
wherein said third region, which is tucked inwardly of said article and toward said waist-hole, defines a concave bottom of said article.

14. The wearing article according to claim 13, wherein said third region is free of absorbent material of said core.

15. The wearing article according to claim 13, wherein said third region is part of a low stiffness zone in which said panel has a stiffness lower than in other zones of said panel.

16. The wearing article according to claim 15, further comprising a pair of fourth folding guides extending from one of said third folding guides, toward one of said front and rear waist regions, and respectively toward transversely opposite side edges of said panel;
wherein said fourth folding guides are also part of said low stiffness zone.

17. The wearing article according to claim 16, further comprising a pair of fifth folding guides extending from the other one of said third folding guides, toward the other one of said front and rear waist regions, and respectively toward the transversely opposite side edges of said panel;
wherein said fifth folding guides are also part of said low stiffness zone.

18. The wearing article according to claim 13, wherein said third region, which is tucked inwardly of said article and toward said waist-hole, is further folded along two auxiliary folding guides which extend diagonally of said third region and intersect each other;
the folded and tucked third region having, at an intersection of said auxiliary folding guides, an apex pointed toward said waist hole.

19. The wearing article according to claim 18, wherein said third region is free of absorbent material of said core.

20. The wearing article according to claim 18, wherein said third region is part of a low stiffness zone in which said panel has a stiffness lower than in other zones of said panel.

* * * * *